(12) United States Patent
Tan et al.

(10) Patent No.: US 10,682,439 B2
(45) Date of Patent: Jun. 16, 2020

(54) THREE-DIMENSIONAL POROUS POLYURETHANE SCAFFOLD FOR REPAIRING CENTRAL NERVE INJURIES AND PREPARATION METHOD THEREOF

(71) Applicant: SICHUAN UNIVERSITY, Chengdu, Sichuan (CN)

(72) Inventors: Hong Tan, Chengdu (CN); Fang Fang, Chengdu (CN); Jiehua Li, Chengdu (CN); Yanchao Wang, Chengdu (CN); Yingke Wu, Chengdu (CN); Qiang Fu, Chengdu (CN); Feng Luo, Chengdu (CN)

(73) Assignee: SICHUAN UNIVERSITY, Chengdu (CN)

( * ) Notice: Subject to any disclaimer, the term of this patent is extended or adjusted under 35 U.S.C. 154(b) by 0 days.

(21) Appl. No.: 16/062,858

(22) PCT Filed: Dec. 13, 2016

(86) PCT No.: PCT/CN2016/109596
§ 371 (c)(1),
(2) Date: Jun. 15, 2018

(87) PCT Pub. No.: WO2017/101754
PCT Pub. Date: Jun. 22, 2017

(65) Prior Publication Data
US 2019/0046685 A1     Feb. 14, 2019

(30) Foreign Application Priority Data
Dec. 17, 2015  (CN) .......................... 2015 1 0947956

(51) Int. Cl.
*A61L 27/18*     (2006.01)
*A61L 27/26*     (2006.01)
(Continued)

(52) U.S. Cl.
CPC ............... *A61L 27/18* (2013.01); *A61L 27/26* (2013.01); *A61L 27/54* (2013.01); *A61L 27/56* (2013.01);
(Continued)

(58) Field of Classification Search
CPC .......... A61L 27/18; A61L 27/26; A61L 27/54; A61L 27/56; A61L 2300/222;
(Continued)

(56) References Cited

U.S. PATENT DOCUMENTS

| 2009/0175921 | A1* | 7/2009 | Gunatillake | A61L 27/18 424/423 |
| 2012/0183622 | A1* | 7/2012 | Guelcher | A61K 9/0024 424/497 |
| 2015/0037387 | A1 | 2/2015 | Coleman et al. | |

FOREIGN PATENT DOCUMENTS

| CN | 101455862 A | 6/2009 |
| CN | 103751852 A | 4/2014 |
| EP | 1 216 717 A1 | 6/2002 |

OTHER PUBLICATIONS

Wang et al., "Waterborne biodegradable polyurethane 3-dimensional porous scaffold for rat cerebral tissue regeneration," RSC Adv., 2016, 6, 3840-3849. (Year: 2016).*

(Continued)

*Primary Examiner* — Aradhana Sasan
(74) *Attorney, Agent, or Firm* — Birch, Stewart, Kolasch & Birch, LLP (57) ABSTRACT

A three-dimensional porous polyurethane scaffold for repairing central nerve injuries and a preparation method are disclosed. The scaffold includes three-dimensional porous polyurethane, wherein the compression modulus of the three-dimensional porous polyurethane is 0.001-10.0 MPa and the pore diameter is 10-200 μm. The three-dimensional porous polyurethane scaffold has an efficient central nerve
(Continued)

repair function without additionally inoculating functional cells or factors and can partially restore the original nerve function of tested animals, the preparation method is simple and it has a great prospect of application.

20 Claims, 4 Drawing Sheets (51) Int. Cl.
 A61L 27/54 (2006.01)
 A61L 27/56 (2006.01)
 C08L 75/04 (2006.01)
 B01D 71/54 (2006.01)
(52) U.S. Cl.
 CPC ....... *C08L 75/04* (2013.01); *A61F 2210/0004* (2013.01); *A61F 2250/0031* (2013.01); *A61F 2250/0067* (2013.01); *A61L 2300/222* (2013.01); *A61L 2300/414* (2013.01); *A61L 2300/604* (2013.01); *A61L 2300/608* (2013.01); *A61L 2430/32* (2013.01); *B01D 71/54* (2013.01); *C08L 2203/02* (2013.01)
(58) Field of Classification Search
 CPC ......... A61L 2300/414; A61L 2300/604; A61L 2300/608; A61L 2430/32; A61L 2300/252; C08L 75/04; C08L 2203/02; A61F 2210/0004; A61F 2250/0031; A61F 2250/0067; A61F 2/02; A61F 2240/002; B01D 71/54
 See application file for complete search history.

(56) References Cited

OTHER PUBLICATIONS

Fawcett et al., "The glial scar and central nervous system repair", Brain Research Bulletin, 1999, vol. 49, No. 6, pp. 377-391.
International Search Report, issued in PCT/CN2016/109596, dated Feb. 9, 2017.
Li, "Application and comparison of various tissue engineered materials in the repair of nerve injury", Journal of Clinical Rehabilitative Tissue Engineering Research, Sep. 17, 2010, vol. 14, No. 38, pp. 7205-7208.
Morelli et al., "Neuronal growth and differentiation on biodegradable membranes", J Tissue Eng Regen Med, 2015, vol. 9, pp. 106-117.
Xu et al., "Fabrication and Evaluation of Polyurethane Scaffolds with Honeycomb-Like Structure", Chinese Journal of Biomedical Engineering, Oct. 2014, vol. 33, No. 5, pp. 593-599.

\* cited by examiner

THREE-DIMENSIONAL POROUS
POLYURETHANE SCAFFOLD FOR
REPAIRING CENTRAL NERVE INJURIES
AND PREPARATION METHOD THEREOF

FIELD OF THE INVENTION

The present invention relates to the field of central nerve injury repair, in particular to a three-dimensional porous polyurethane scaffold for repairing central nerve injuries and a preparation method thereof.

BACKGROUND OF THE INVENTION

Generally, the regeneration ability of adult's nervous systems is limited. As a result, different extents of losses in sensory or movement functions and neuropathic pains will be caused once people suffer nerve injuries.

Nerve transplantation is a "Golden Rule" for treating nerve injuries at current. However, due to shortage of donors and certain risks in surgeries, it is very difficult to popularize this treatment approach. More importantly, its treatment effect is not very satisfactory.

It is highly concerned in recent years to promote repair of damaged nerves by using tissue engineering technology, especially by using artificial nerve tissue engineering scaffolds, and a series of eye-striking achievements are obtained.

However, current researches mainly focus on the aspect of low-difficulty peripheral nerve repair. There are few researches on the aspect of high-difficulty central nerve repair. This is because the regeneration ability of the central nervous system is obviously weaker than the regeneration ability of the peripheral nervous system (J. W. Fawcett, R. A. Asher, The glial scar and central nervous system repair, Brain Res. Bull. 49 (1999) 377-391). At the same time, after central nerve fibers are damaged, it is considered that they cannot be regenerated at present (Sabrina Morelli, Antonella Piscioneri, Neuronal growth and differentiation on biodegradable membranes, J Tissue Eng Regen Med (2012)). Therefore, methods applicable to repairing the peripheral nervous system at present are almost not applicable to repairing the central nervous system. As a result, no major breakthrough has been made in many years in researches on repairing damaged central nerves by using the existing tissue engineering technology. However, by comparison, remarkable effects have already been achieved in the aspect of repairing the peripheral nervous system by using tissue engineering scaffolds.

In researches on repairing the peripheral nervous system by using artificial nervous tissue engineering scaffolds, people find that the repair possibility of nerves depends on factors such as scaffold structure and chemical or biological induced stimulation, scaffolds such as hollow tubes and electrospun fiber membranes are prepared under this finding by using degradable natural macromolecular materials (such as collagen, chitosan and alginate) and synthetic degradable materials (such as polylactic acid-polyglycollic acid copolymer, polycaprolactone and polypyrrole), and certain peripheral nerve repair effects are achieved. On this basis, by inoculating some functional cells (such as Schwann cells, olfactory ensheathing cells and neural stem cells) or growth factors (such as nerve growth factors, brain-derived neurotrophic factors and glia-derived neurotrophic factors), better peripheral nerve repair effects are realized.

However, in regard to the repair of the central nervous system, no applicable artificial nerve tissue engineering scaffolds with remarkable effects have been found. As reported at present, researchers generally use gel only for a scaffold for repairing the central nervous system, and a certain effect can be achieved only under the joint effect of the inoculated cells and carried factors. It is worthy of being pointed out that the holding time of the gel scaffold in vivo is very short and a long-time repair effect cannot be provided. More importantly, as known up to now, any current research achievements cannot enable the original nerve function of tested animals to be restored. In other words, the current research achievements mainly stay at a level of in-vitro experiments, and it is still a major challenge in researches in this field to find a central nervous system repairing scaffold which has an actual application value.

In order to overcome the disadvantage that the holding time of gel is short, researchers try to use polyhydroxyalkanoate (PHA) three-dimensional nano-fibers as a scaffold for repairing the central nervous system, and the obtained achievement solves the problem that the holding time of the scaffold is short to a certain extent. However, the repair effect thereof depends on the inoculated neural stem cells (NSCs). More importantly, it still stays at a level of in-vitro experiments and no obvious practical prospect is shown.

For the medical field, when the practical prospect of a certain technology is judged, it is a fundamental indicator whether the in-vivo experiment result is effective and the repeatability is good. For cell-containing scaffolds, since the exertion of the function of cells is greatly influenced by the environment, in the process that the scaffold is implanted and the effect is shown after the scaffold is implanted, the implantation operation steps, the surrounding environment of implantation parts and the physiological environment therein will all influence the superiority of the repair effect. Therefore, the existing central nervous system repair methods not only do not show any expectable excellent animal experiment results, but also are very difficult to implement.

To sum up, it is urgent to find a tissue engineering scaffold for repairing the central nervous system, which can repair damaged central nerves, has good animal experiment effects and has a low difficulty in implementation.

SUMMARY OF THE INVENTION

In view of the disadvantage of the prior art, one purpose of the present invention is to provide a three-dimensional porous polyurethane scaffold for repairing central nerve injuries. The three-dimensional porous polyurethane scaffold can promote adhesion, crawling and growth of nerve cells and remodeling of synapses, more importantly can restore partial original nerve functions of tested animals suffering central nerve injuries, and solves the major technical problem that the functions of the damaged central nerves cannot be restored purely depending on scaffolds in the prior art.

The scaffold comprises three-dimensional porous polyurethane, and the compression modulus of the three-dimensional porous polyurethane is 0.001-10.0 MPa; and the pore diameter is 10-200 μm.

If central nerves are repaired by using a tissue engineering scaffold which is usually used for repairing peripheral nerves, as proved by years of experiments, it is difficult to obtain satisfactory effects. This is because, after central nerves are damaged, an environment which inhibits nerve regeneration is produced around the damaged central nerves and the repair of the damaged central nerves is inhibited. At present, in-vitro experiments which have effects of repairing central nerves mainly focus on researches on chitosan gel scaffolds carrying relevant cells and factors, and there are a rarely few of reports about researches which have good in-vivo repair effects (mainly repair effects of original nerve functions).

Polyurethane has very good biocompatibility, is widely applied in aspects such as medicine controlled release and tissue engineering scaffolds, and is always widely used for researches on repair of damaged peripheral nervous systems. In the aspect of the repair of the central nervous system, on Aug. 17, 2015, Biomaterials, a famous magazine in this field, discloses a research on repairing a damaged central nervous system of zebra fish by using heat-sensitive polyurethane gel carrying nerve stem cells, and a good effect was achieved. However, zebra fish is just a lower living being and its germ line is greatly different from that of mammals. In addition, this research merely overcomes the disadvantage that the elasticity is low or the workability is low when materials such as PLA, PLGA or PCL are used as scaffolds, and overcomes the disadvantage that the mechanical strength is low when natural macromolecules are used. Beside these, it makes no further breakthrough contribution to this field and repairs damaged central nerves still depending on nerve stem cells.

After a great number of long-time exploring researches, the inventor of the present invention amazingly finds that damaged central nerves can be very well repaired by using a scaffold containing three-dimensional porous polyurethane with compression modulus of 0.001-10.0 MPa and pore diameter of 10-200 μm. It is more worthy of being mentioned that partial original nerve functions (especially movement functions) of tested animals suffering central nerve damages can be directly restored. The present invention not only overcomes the disadvantages that the holding time of gel in vivo is short, the cell inoculation operation is complex and it is easy influenced by the environment, but also remarkably improves the effect of repairing the central nervous system and can enable partial movement functions of tested animals to be restored.

Up to now, the mechanism of the present invention in the aspect of the repair of the damaged central nerves is not fully clear and is still under research.

Obviously, the present invention makes the following contribution to this field: providing a tissue engineering scaffold which overcomes the disadvantages that the holding time is short, the operation difficulty is great and it is easy influenced by the environment in the prior art, and which has a prominent effect of repairing the damaged central nervous system.

As a preferred solution, the compression modulus of the three-dimensional porous polyurethane is 0.01-7.0 MPa; and more preferably, the compression modulus of the three-dimensional porous polyurethane is 0.1-3.0 MP.

As a preferred solution, the pore diameter of the three-dimensional porous polyurethane is 20-150 μm.

The porosity of the three-dimensional porous polyurethane is 30-95%, and preferably 70-90%.

For the repair of the nervous system, the mechanical performance, the pore diameter and the porosity of the scaffold play a vital role.

Theoretically, if the compression modulus of the scaffold is too low, the role of supporting cell growth cannot be played; and if the compression modulus is too high, damages are easily caused to surrounding tissues. At the same time, if the pore diameter of the scaffold is too small, cells cannot easily enter; and if the pore diameter is too large, the number of sites for cell adhesion becomes smaller and the growth of the cells is not facilitated. In addition, if the porosity of the scaffold is too low, nutrient transmission between cells and mutual growth signals are obstructed and the growth of the cells is not facilitated; and if the porosity of the scaffold is too high, the mechanical performance of the material is too poor and the effect of supporting cell growth cannot be played.

Regardless of the repair of the peripheral nervous system or the central nerves, the above-mentioned recognition has already been common knowledge in this field. However, for many years, researchers in this field still cannot realize the repair of the damaged central nerves by merely adjusting the compression modulus, the pore diameter and the porosity of the scaffold. Although the effect of the scaffold of the present invention in repairing the damaged central nerves is better when the compression modulus, the pore diameter and the porosity of the three-dimensional porous polyurethane are in respective preferred ranges, the mechanism thereof still needs to be further investigated.

The structure of the three-dimensional porous polyurethane comprises one of polyurethane electrospun fiber porous scaffold, polyurethane freeze-dried porous scaffold, polyurethane 3D printed porous scaffold, polyurethane particulate leached porous scaffold and polyurethane gas foamed porous scaffold.

Preferably, the scaffold further comprises a functional cell factor and/or a functional cell; and the functional cell factor comprises at least one of nerve growth factor, brain-derived neurotrophic factor and glia-derived neurotrophic factor.

Inoculation of the functional cell factor and/or functional cell can enable the repair effect of the central nervous system to be further improved. However, it is worthy of being mentioned that the three-dimensional porous polyurethane in the scaffold of the present invention is a key to the excellent effect achieved by the present invention, the addition of the functional cell factor and/or functional cell merely plays a role of further improving the repair effect on the basis of the excellent effect which has already been achieved, and it shall not be understood as that the addition of the functional cell factor and/or functional cell is indispensable for the production of the technical effect of the present invention.

The central nerve injuries comprise one of brain injury, spinal nerve injury and retina injury.

Another purpose of the present invention is to provide a method for preparing a three-dimensional porous polyurethane scaffold for repairing central nerve injuries, and the method comprises the following step:

preparing the three-dimensional porous polyurethane scaffold by using a raw material at least containing polyurethane, the used preparation method comprising one of freeze-drying method, electrostatic spinning method, 3D printing method, particulate leaching method and gas foaming method; and the polyurethane comprising biodegradable polyurethane, and the biodegradable polyurethane comprising thermoplastic biodegradable polyurethane or crosslinked biodegradable polyurethane.

The operation process of the freeze-drying method comprises: storing polyurethane emulsion at 4° C. for 4 h and removing gas in the emulsion; then standing at −20° C. for a night and then performing freeze-drying for 2 d; and then performing drying.

The operation process of the electrostatic spinning method comprises: dissolving polyurethane in a mixed solvent of tetrahydrofuran and dimethylacetamide or in hexafluoroisopropanol, and performing electrospinning by using tin foil paper as a receiver to obtain a polyurethane electrospun fiber porous scaffold.

The operation process of the 3D printing method comprises: adding gelatin into polyurethane emulsion and performing 3D printing to obtain a polyurethane 3D printed porous scaffold.

The operation process of the particulate leaching method comprises: adding sodium chloride into polyurethane emulsion, then spreading solution on a smooth plane, allowing natural volatilization and then performing drying; and then using water to wash away sodium chloride particulates thereof to obtain a polyurethane particulate leached porous scaffold.

The operation process of the gas foaming method comprises: drying polyurethane solution to obtain a thin film, then immersing the obtained thin film in supercritical carbon dioxide to a saturated state and finally decreasing pressure to a normal-pressure state to obtain a polyurethane gas foamed porous scaffold.

As a preferred solution, the raw material further comprises a functional cell factor and/or a functional cell; and the functional cell factor comprises at least one of nerve growth factor, brain-derived neurotrophic factor and glia-derived neurotrophic factor.

Another purpose of the present invention is to provide application of the above-mentioned three-dimensional porous polyurethane to repair of central nerve injuries.

The present invention has the following beneficial effects:

1. The three-dimensional porous polyurethane provided by the present invention has an efficient central nerve repair function without additionally inoculating functional cells or factors and can partially restore the original nerve function of tested animals.

2. The method for preparing the three-dimensional porous polyurethane provided by the present invention is simple.

3. The method for using the three-dimensional porous polyurethane provided by the present invention is simple and the application prospect is great.

BRIEF DESCRIPTION OF THE DRAWINGS

FIG. 3 illustrates morphology before and after a porous polyurethane scaffold provided by the present invention is implanted in a model used by the present invention, wherein A: a situation in an operation of implanting a freeze-dried three-dimensional porous crosslinked biodegradable polyurethane scaffold in a rat, wherein the position of a dashed box is a position at which the scaffold is implanted; B: a situation in an operation of implanting normal saline in a rat in a comparative example; C: brain morphology after 8 weeks after the freeze-dried three-dimensional porous crosslinked biodegradable polyurethane scaffold is implanted in the rat, wherein the position of a dashed box is a position at which the scaffold is implanted; and D: brain morphology after 8 weeks after normal saline is implanted in the rat in the comparative example, wherein the position of a dashed box is a position at which the normal saline is implanted.

DETAILED DESCRIPTION OF THE EMBODIMENTS

The present invention will be described below in detail through Examples. It is necessary to point out that the following Examples are just used for further describing the present invention and shall not be understood as limitations to the scope of the present invention. Some nonessential improvements and adjustments made by one skilled in the art according to the summary of the invention are still included in the scope of the present invention.

EXAMPLE 1

Figure 1:
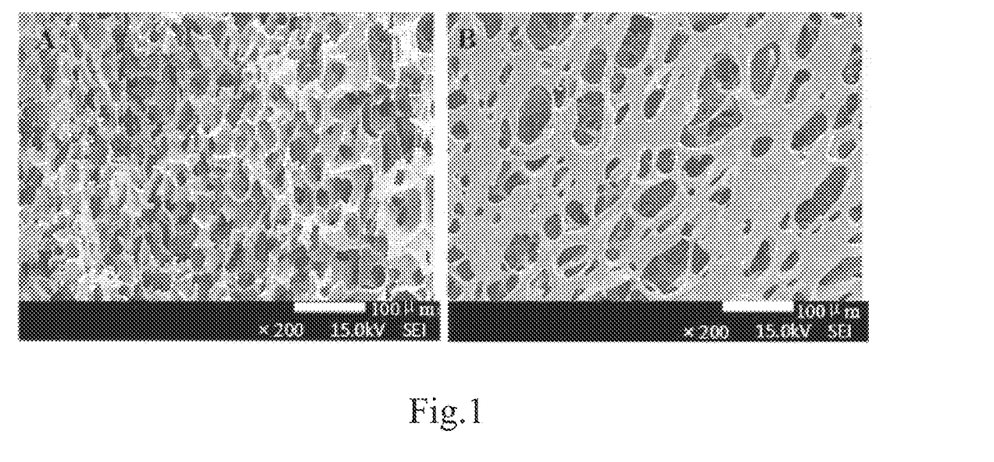
FIG. 1 illustrates SEM morphology characterization results of a three-dimensional porous polyurethane scaffold provided by the present invention, wherein A: section morphology of a freeze-dried three-dimensional porous crosslinked biodegradable polyurethane scaffold; and B: surface morphology of a freeze-dried three-dimensional porous crosslinked biodegradable polyurethane scaffold.

Crosslinked biodegradable polyurethane aqueous emulsion was stored at 4° C. for 4 h and gas in the emulsion was removed; then the emulsion was stood at −20° C. for a night and then freeze-drying was performed for 24 h; and then drying was performed at 40° C. to obtain a freeze-dried three-dimensional porous polyurethane scaffold. Average pore diameter of the freeze-dried three-dimensional porous polyurethane scaffold was 80 μm, the porosity was 90%, the compression modulus was 1.0 MPa and the structure was as illustrated in FIG. 1. The freeze-dried three-dimensional porous crosslinked biodegradable polyurethane scaffold was used for repairing regeneration functions of rat brain axons and synapses.

EXAMPLE 2

Thermoplastic biodegradable polyurethane was dissolved in dimethyl sulfoxide to prepare solution with mass concentration of 30%, the solution was stored at 4° C. for 4 h and gas in the solution was removed; and then the solution was stood at −20° C. for a night and then freeze-drying was performed for 24 h to obtain a freeze-dried three-dimensional porous polyurethane scaffold. Average pore diameter of the freeze-dried three-dimensional porous polyurethane scaffold was 150 μm, the porosity was 70% and the compression modulus was 3.0 MPa. The freeze-dried three-dimensional porous thermoplastic biodegradable polyurethane scaffold was used for repairing regeneration functions of rat brain axons and synapses.

EXAMPLE 3

Sodium chloride with mass ratio of 40% was added into in crosslinked biodegradable polyurethane emulsion, then the emulsion was spread on a smooth plane, natural volatilization was allowed for 4 d, and then drying was performed; and then water was used to wash away sodium chloride particulates thereof to obtain a particulate leached three-dimensional porous crosslinked biodegradable polyurethane scaffold. Average pore diameter of the particulate leached three-dimensional porous crosslinked biodegradable polyurethane scaffold was 200 μm, the porosity was 30% and the compression modulus was 7.0 MPa. The particulate leached three-dimensional porous crosslinked biodegradable polyurethane scaffold was used for repairing regeneration functions of rat brain axons and synapses.

EXAMPLE 4

Thermoplastic biodegradable polyurethane was dissolved in a mixed solvent of tetrahydrofuran and dimethylacetamide, tin foil paper was used as a receiver, electrospinning voltage was set to 20 kv, a receiving distance was set to 15 cm, a flow rate was set to 1 ml/h and electrospinning was performed to obtain a thermoplastic biodegradable polyurethane electrospun fiber scaffold. Average pore diameter of the thermoplastic biodegradable polyurethane electrospun fiber scaffold was 100 μm, the porosity was 85% and the compression modulus was 0.001 MPa. The electrospun fiber thermoplastic biodegradable polyurethane scaffold was used for repairing regeneration functions of rat brain axons and synapses.

EXAMPLE 5

Thermoplastic biodegradable polyurethane solution was dried to obtain a thin film, then the obtained thin film was immersed in supercritical carbon dioxide to a saturated state and finally pressure was decreased to a normal-pressure state to obtain a gas foamed three-dimensional porous thermoplastic biodegradable polyurethane scaffold. Average pore diameter of the gas foamed three-dimensional porous thermoplastic biodegradable polyurethane scaffold was 20 μm, the porosity was 40% and the compression modulus was 10.0 MPa. The gas foamed three-dimensional porous thermoplastic biodegradable polyurethane scaffold was used for repairing regeneration functions of rat brain axons and synapses.

EXAMPLE 6

Thermoplastic biodegradable polyurethane was dissolved in a mixed solvent of tetrahydrofuran and dimethylacetamide, tin foil paper was used as a receiver, electrospinning voltage was set to 15 kv, a receiving distance was set to 10 cm, a flow rate was set to 0.5 ml/h and electrospinning was performed to obtain an electrospun fiber thermoplastic biodegradable polyurethane scaffold. Average pore diameter of the electrospun fiber thermoplastic biodegradable polyurethane scaffold was 10 μm, the porosity was 85% and the compression modulus was 0.01 MPa. The thermoplastic biodegradable polyurethane electrospun fiber scaffold was used for repairing regeneration functions of rat brain axons and synapses.

EXAMPLE 7

Nerve growth factors were added into crosslinked biodegradable polyurethane emulsion, the emulsion was stored at 4° C. for 4 h and gas in the emulsion was removed; then the emulsion was stood at −20° C. for a night and then freeze-drying was performed for 24 h; and then drying was performed at 40° C. by using a drying oven to obtain a freeze-dried three-dimensional porous polyurethane scaffold containing growth factors. Average pore diameter of the freeze-dried three-dimensional porous polyurethane scaffold containing growth factors was 80 μm, the porosity was 85% and the compression modulus was 1.0 MPa. The scaffold added with nerve growth factors was used for repairing regeneration functions of rat brain axons and synapses.

EXPERIMENTAL EXAMPLE

Relevant experiments were carried out to the three-dimensional porous polyurethane scaffolds obtained in Examples 1-7, and specific experiments contents are as follows:
II. Animal Experiments
(I) Establishment of Animal Model
Adult SD rats were anesthetized by using 10% chloral hydrate (0.05 ml/100 g), hairs on heads were shaved after anesthetization, the head of each rat was cut open from the center, a bregma was found, a bone window with a size of 5*4 mm was opened at the front of the bregma, a dura mater was removed, and then an M1 segment with a size of 4 mm*4 mm*3 mm was excavated. After bleeding was fully stopped, the three-dimensional porous biodegradable polyurethane scaffolds obtained in Examples 1-7 were respectively implanted, the bone window was not necessarily blocked and skins were sutured after bleeding was stopped. After operation, cefathiamidine (0.05 g/d) was continuously injected for 3 d to prevent infection. Restoration situations of movement functions of fore limbs were observed after 2, 4 and 8 weeks after the M1 segments of the rats were excised and the three-dimensional porous polyurethane scaffolds were implanted, scoring was performed and then the rats were executed.

Comparative example: a method for establishing a rat craniocerebral injury model was the same as the method for establishing the animal model in the Examples, except that normal saline was used for replacing the polyurethane scaffolds and filled into brain tissues after the model was established, other operation processes were all the same, the rats were fed by adopting the same environment, and identically, after 2, 4 and 8 weeks after the scaffolds were implanted in the Examples, restoration situations of movement functions of fore limbs of the rats in a control group were observed, scoring was performed and then the rats were executed.

(II) Function Evaluation
Since the M1 segment of each rat was excised in the experiment and the function of this segment was mainly movement of fore limbs, Bederson scoring standards were introduced to perform experimental result evaluation. Scoring standards are as shown in Table 1 and are specifically as follows: each rat was lifted up from a tail to a position 1 m above the ground, upper limbs on both sides were observed, it is considered as non-paralyzed and scored 0 point if two upper limbs both pointed to the ground, and it scored 1 point if a side opposite to the side of the operation was continuously contracted, the rat which scored 1 point was placed on a ground with full friction force to guarantee that claws of the rat can tightly grasp the ground, the rat was slightly lifted up from the tail, lateral force was applied from all directions till the fore limbs slid for a certain distance, and it scored 2 points if an affected side presented a decrease in lateral force resistance; and the rat which scored 2 points was allowed to freely move, and it scored 3 points if the rat made circular movement.

TABLE 1

| Score | Presentation | Meaning |
|---|---|---|
| 0 | Each rats was lifted up from tails to a position 1 m above the ground, upper limbs on both sides were observed, and two upper limbs of the rat both pointed to the ground. | Normal rat (non-paralyzed) |
| 1 | A side opposite to the side of the operation was continuously contracted, i.e., an upper limb of one side of the rat was contracted and the upper limb of the other side pointed to the ground. | Slightly paralyzed |
| 2 | The rat was placed on a ground with full friction force to guarantee that claws of the rat can tightly grasp the ground, the rat was slightly lifted up from the tail, lateral force was applied from all directions till the fore limbs slid for a certain distance, and an affected side presented a decrease in lateral force resistance, i.e., a decrease in resistance to horizontal force. | Moderately paralyzed |
| 3 | The rat made circular movement. | Seriously paralyzed |

Bederson scoring method was adopted for evaluating movement functions of front limbs of rats after 2, 4 and 8 weeks after M1 segments of the rats were excised and the three-dimensional porous polyurethane scaffolds obtained in Examples 1-7 were implanted.

Figure 2:
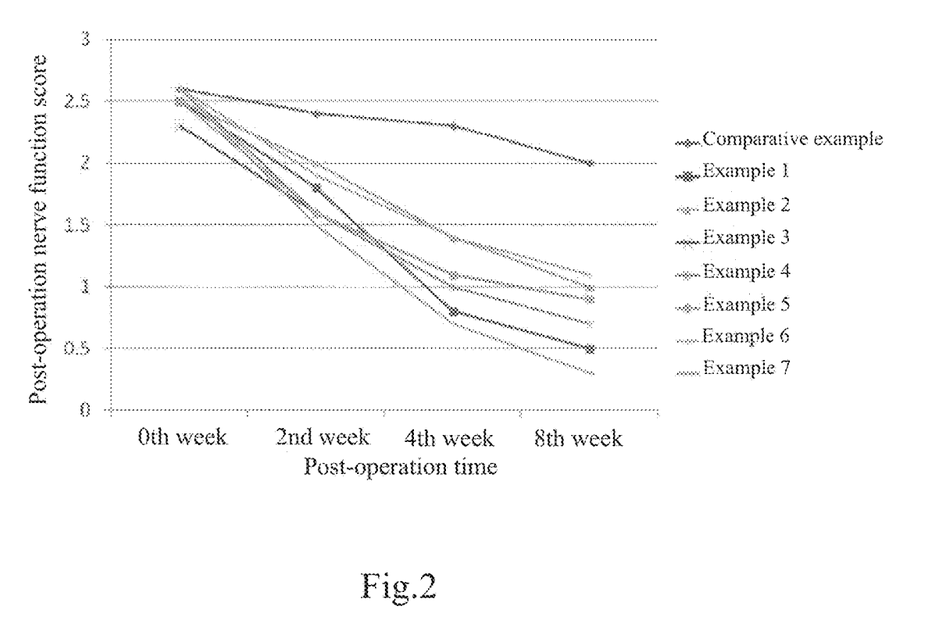
FIG. 2 illustrates post-operation rat nerve function score results in a model used by the present invention.

As illustrated in FIG. 2, an average value of nerve function scores in all Examples of the present invention was obviously decreased relative to the comparative example. As shown by results, after 8 weeks after the freeze-dried three-dimensional porous crosslinked biodegradable polyurethane scaffold with average pore diameter of 80 μm, porosity of 90% and compression modulus of 1.0 MPa in Example 1 was implanted into the rats, the average Bederson score was 1.5 lower than that of the comparative example. After 8 weeks after the freeze-dried three-dimensional porous thermoplastic biodegradable polyurethane scaffold with average pore diameter of 150 μm, porosity of 70% and compression modulus of 3.0 MPa in Example 2 was implanted into the rats, the average Bederson score was 1.0 lower than that of the comparative example. After 8 weeks after the particulate leached three-dimensional porous crosslinked biodegradable polyurethane scaffold with average pore diameter of 200 μm, porosity of 30% and compression modulus of 7.0 MPa in Example 3 was implanted into the rats, the average Bederson score was 1.1 lower than that of the comparative example. After 8 weeks after the electrospun fiber thermoplastic biodegradable polyurethane scaffold with average pore diameter of 100 μm, porosity of 85% and compression modulus of 0.001 MPa in Example 4 was implanted into the rats, the average Bederson score was 1.3 lower than that of the comparative example. After 8 weeks after the gas foamed three-dimensional porous thermoplastic biodegradable polyurethane scaffold with average pore diameter of 20 μm, porosity of 40% and compression modulus of 10.0 MPa in Example 5 was implanted into the rats, the average Bederson score was 1.1 lower than that of the comparative example. After 8 weeks after the electrospun fiber thermoplastic biodegradable polyurethane scaffold with average pore diameter of 10 μm, porosity of 85% and compression modulus of 0.01 MPa in Example 6 was implanted into the rats, the average Bederson score was 0.9 lower than that of the comparative example. After 8 weeks after the freeze-dried three-dimensional porous crosslinked biodegradable polyurethane scaffold added with nerve growth factors and with average pore diameter of 80 μm, porosity of 85% and compression modulus of 1.0 MPa in Example 7 was implanted into the rats, the average Bederson score was 1.7 lower than that of the comparative example.

As proved by the above-mentioned results, the three-dimensional porous polyurethane scaffolds obtained in all Examples of the present invention can very well partially restore movement functions of fore limbs of rats, and the repair effect of the scaffold added with the nerve growth factors is better.

Figure 3:
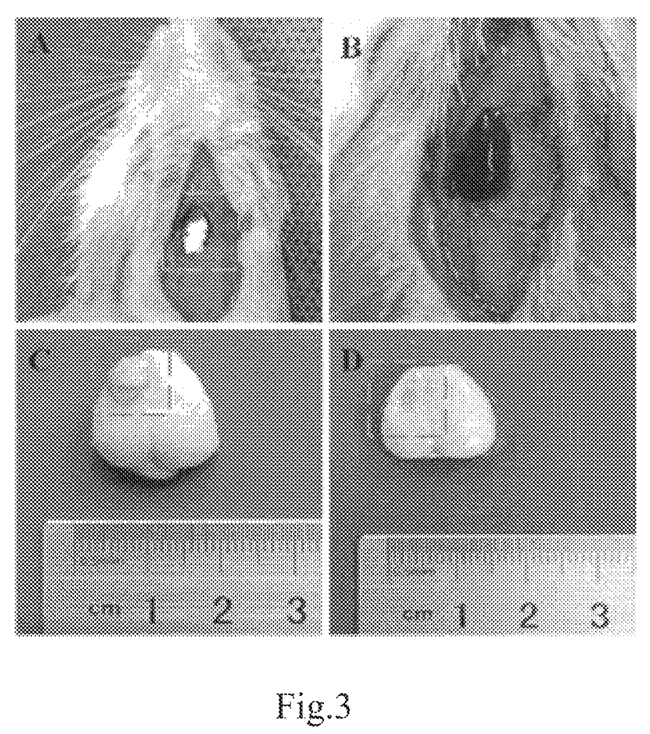

FIG. 3 is images showing an operation method employed when the three-dimensional porous polyurethane scaffolds are implanted in the rats and an operation method employed in the comparative example, and simultaneously illustrates an in-vivo situation after 8 weeks after the three-dimensional porous polyurethane scaffolds are implanted and an in-vivo situation in the comparative example. As shown by results, as compared with the comparative example, the three-dimensional porous polyurethane scaffolds provided by the present invention have enough strength to maintain the completeness of the scaffolds in the operation process to support cell infiltration, axon regeneration and synapse reconstruction.

(III) Histological Evaluation

The rats were executed after scores were recorded, PBS was perfused into brain tissues, then the brain tissues were taken out, a filling material was taken and partially quick-frozen in OCT gelatin at −80° C., cutting was performed to obtain 5 μm sections, the sections were fixed for 1 h by using 4% paraformaldehyde and then the sections were washed twice by using PBS; perforation was performed for 15 min by using 0.3% Trition X-100, washing was performed for one time by using PBS and then blocking was performed for 1 h at room temperature by using an antigen blocking solution; washing was performed twice by using PBS, then primary antibodies were added and standing was performed at 4° C. for a night; washing was performed twice by using PBS, then secondary antibodies were added, room-temperature incubation was performed for 1 h, washing was performed twice by using PBS and DAP1 was added for staining for 15 min; and the sections were blocked by using an anti-fluorescent quenching agent and observation was performed on the next day under a confocal laser scanning microscope.

Notes: primary antibodies in this experiment are anti-GAP43 antibodies and anti-synaptophysin antibodies. GAP43 is a well-recognized nerve regeneration sign and is highly expressed during axon regeneration and synapse formation. Synaptophysin is considered as a reliable sign representing synapses.

Figure 4:
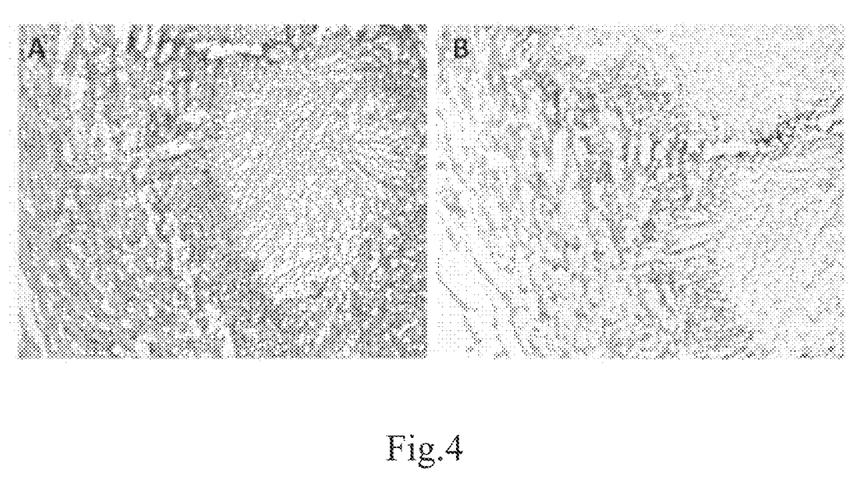
FIG. 4 is images showing HE staining result of brain tissue frozen section after 4 weeks after a scaffold is implanted in a model used by Example 1 of the present invention, wherein image A is a ×100 enlarged image and image B is a ×200 enlarged image.
Figure 5:
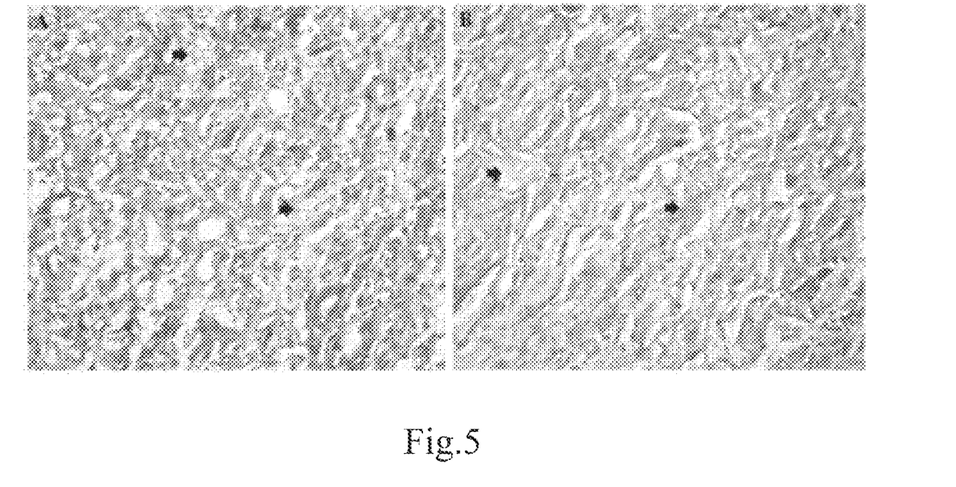
FIG. 5 is images showing HE staining result of brain tissue paraffin section after 8 weeks after a scaffold is implanted in a model used by Example 1 of the present invention, wherein image A is a ×400 enlarged result image and illustrates a situation of an edge of a regenerated part of the scaffold, wherein positions shown by arrows are degraded scaffolds, and image B is a ×400 enlarged result image and illustrates a situation of a center of a regenerated part of the scaffold, wherein positions shown by arrows are degraded scaffolds.

As illustrated in FIG. 4 and FIG. 5, HE staining results show that the edges of the scaffold provided by the present invention rapidly grew to the center of the scaffold, the blood vessel also entered the scaffold and no inflammation or adverse tissue reaction occurred.

Figure 6:
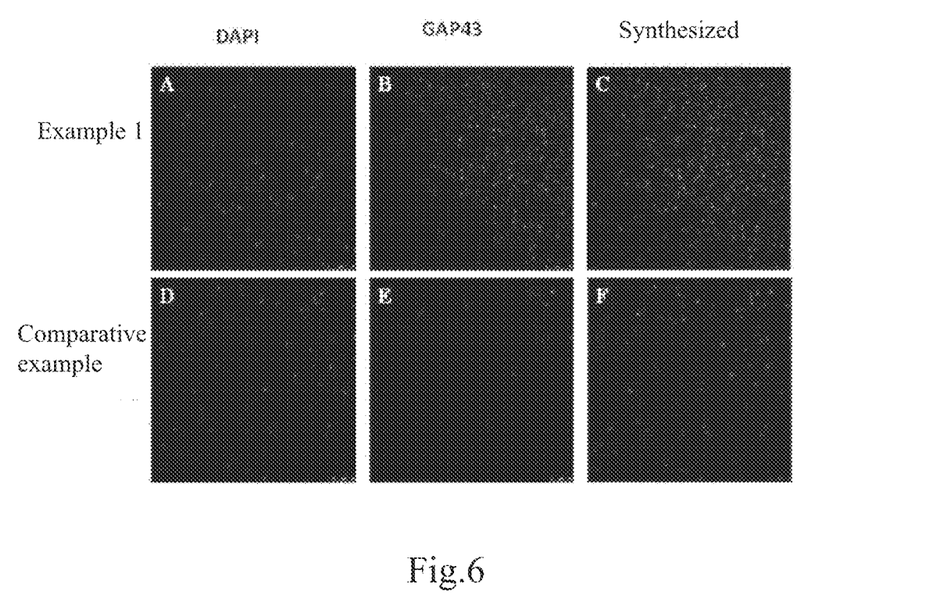
FIG. 6 is images showing confocal laser scanning result of axon regeneration effects in a model used by the present invention, wherein A: a brain tissue cell nucleus in Example 1; B: a post-operation 4th week expression situation of GAP43 in Example 1; C: a cell nucleus and GAP43 synthesis image in Example 1; D: a brain tissue cell nucleus in a comparative example; E: a post-operation 4th week expression situation of GAP43 in a comparative example; and F: a cell nucleus and GAP43 synthesis image in a comparative example.
Figure 7:
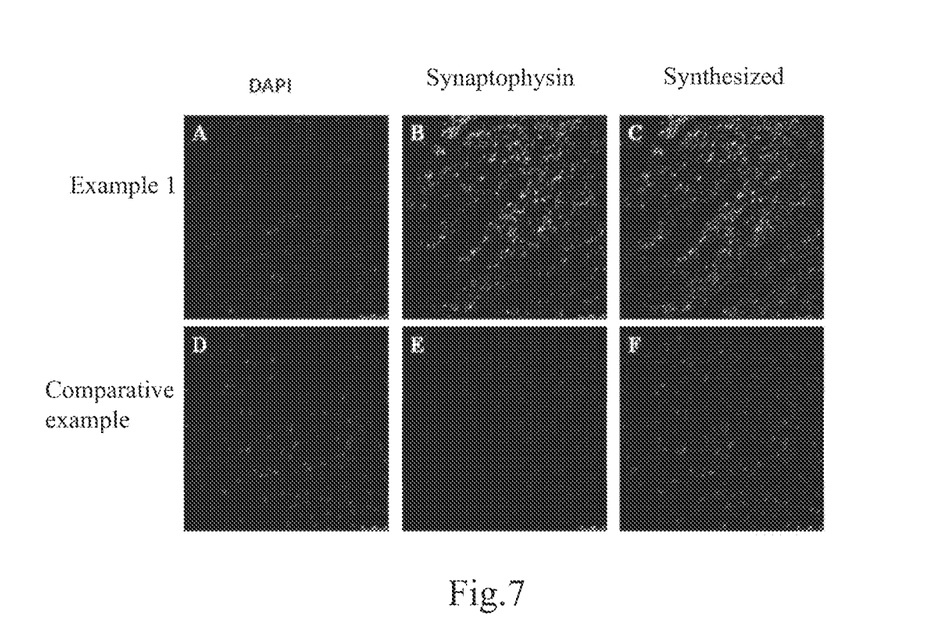
FIG. 7 is images showing confocal laser scanning result of synapse reconstruction effects in a model used by the present invention, wherein A: a brain tissue cell nucleus in Example 1; B: a post-operation 8th week expression situation of synaptophysin in Example 1; C: a cell nucleus and synaptophysin synthesis image in Example 1; D: a brain tissue cell nucleus in a comparative example; E: a post-operation 8th week expression situation of synaptophysin in a comparative example; and F: a cell nucleus and synaptophysin synthesis image in a comparative example.

As illustrated in FIG. 6 and FIG. 7, by using the three-dimensional porous polyurethane provided by the present invention as the scaffold, at the 4th week after the operation, GAP43 was expressed in a great amount, and at the 8th week after the operation, synaptophysin was also expressed in a great amount and it showed that axons and synapses were repaired and reconstructed.

(IV) Western Hybridization

Rat brain tissues after perfusion were taken, a filling material was selected and partially ground in liquid nitrogen and RIPA+PMSF (5 μLmL) were used for digesting tissue powder for 30 min. Centrifugation was performed for 5 min at 4° C. and 12000 rpm. Protein content was determined, and then loading buffer was added for boiling for 10 min at 100° C. A glass plate was cleaned, then 4% stacking gel was prepared, TEMED was added and then the gel was immediately perfused. After the stacking gel was solidified, the gel was put in an electrophoresis tank, enough electrophoresis solution was added and then samples were loaded. Voltage was set to be 120V to perform electrophoresis for 1 h. Six pieces of 7.0-8.3 cm filter paper and one piece of 7.3-8.6 cm nitrocellulose membrane were prepared, clips were put into a transfer tank and transfer was performed for 2 h by using 60V or transfer was performed for 3 h by using 40V, and the membrane was air-dried for use in future. The membrane was wetted from bottom to top by using TBS, then the membrane was moved into a plate containing blocking solution (5% degreased milk), and shaking for blocking for 2 h was performed on a shaker at room temperature; primary antibodies were diluted to proper concentration, the membrane and the antibodies were incubated for a night at 4° C., washing was performed for three times on the shaker at room temperature by using TBST and the time was kept to be 10 min each time; secondary antibodies were diluted to proper concentration and were in contact with the membrane, incubation was performed for 1-2 h at room temperature, washing was performed for three times on the shaker at room temperature by using TBST and the time is kept to be 10 min each time; reagents A and B of ECL were mixed; the mixture was in full contact with the side on which a membrane protein side is located for 1-2 min, then residual solution was fully removed, and the film was packed and put in X-ray film clips; in a dark room, 1× developing solution and fixing solution were respectively poured into a plastic tray; the X-ray film was taken out under red light and was cut to proper size by using a paper cutter; the X-ray film clips were opened, the X-ray film was put on the membrane, the X-ray film clips were closed and timing was started; and exposure time was properly adjusted according to the intensity of signals and was generally 1 min or 5 min. After exposure was completed, the X-ray film clips were opened, the X-ray film was taken out and was rapidly immersed in developing solution for development, and development was stopped immediately after obvious stripes appeared. The development time was generally 1-2 min (20-50° C.) and the development time needed to be prolonged when the temperature was too low (lower than 16° C.). After the development was completed, the X-ray film was immediately immersed in fixing solution, the fixing time was generally 5-10 min till the rubber film became transparent; residual fixing solution was washed away by using tap water and the rubber film was air-dried at room temperature; and the rubber film was scanned or photographed and a gel image processing system was used for analyzing molecular weights and net optical density values of target belts.

Notes: primary antibodies in this experiment are anti-GAP43 antibodies and anti-synaptophysin antibodies. GAP43 is a well-recognized nerve regeneration sign and is highly expressed during axon regeneration and synapse formation. Synaptophysin is considered as a reliable sign representing synapses.

Figure 8:
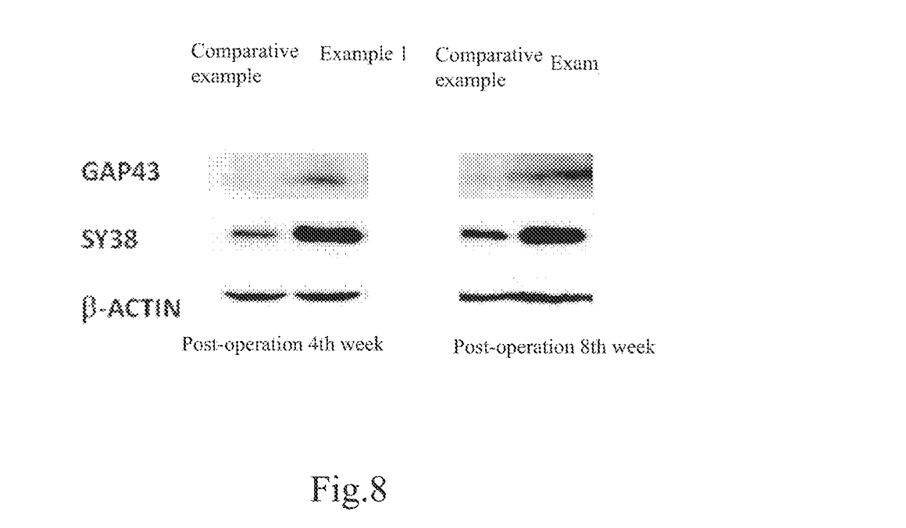
FIG. 8 illustrates Western hybridization experiment result of GAP43 and synaptophysin.

Western hybridization experiment results can prove the expression results of synaptophysin and GAP43 after the scaffold provided by the present invention was implanted. As illustrated in FIG. 8, as compared with the comparative example, the nerve axon regeneration functions in the Examples are obviously restored.

The invention claimed is:

1. A method for preparing a three-dimensional porous polyurethane scaffold for repairing central nerve injuries, comprising:
   preparing the scaffold with three-dimensional porous polyurethane, wherein the compression modulus of the three-dimensional porous polyurethane is 0.001-10.0 MPa; and the pore diameter of the three-dimensional porous polyurethane is 10-200 μm.

2. The method according to claim 1, wherein the compression modulus of the three-dimensional porous polyurethane is 0.01-7.0 MPa; and the pore diameter of the three-dimensional porous polyurethane is 20-150 μm.

3. The method according to claim 1, wherein the compression modulus of the three-dimensional porous polyurethane is 0.1-3.0 MPa.

4. The method according to claim 1, wherein the porosity of the three-dimensional porous polyurethane is 30-95%.

5. The method according to claim 3, wherein the porosity of the three-dimensional porous polyurethane is 30-95%.

6. The method according to claim 4, wherein the porosity of the three-dimensional porous polyurethane is 70-90%.

7. The method according to claim 1, wherein the polyurethane comprises biodegradable polyurethane; and the biodegradable polyurethane comprises thermoplastic biodegradable polyurethane or crosslinked biodegradable polyurethane.

8. The method according to claim 1, wherein the scaffold further comprises a functional cell factor and/or a functional cell; and the functional cell factor comprises at least one of nerve growth factor, brain-derived neurotrophic factor and glia-derived neurotrophic factor.

9. The method according to claim 1, wherein the three-dimensional porous polyurethane scaffold comprises one of polyurethane electrospun fiber porous scaffold, polyurethane freeze-dried porous scaffold, polyurethane 3D printed porous scaffold, polyurethane particulate leached porous scaffold and polyurethane gas foamed porous scaffold.

10. The method according to claim 1, wherein the central nerve injuries comprise one of brain injury, spinal nerve injury and optic nerve injury.

11. The method for preparing the three-dimensional porous polyurethane scaffold according to claim 1, comprises one of freeze-drying method, electrostatic spinning method, 3D printing method, particulate leaching method and gas foaming method; and the polyurethane comprises biodegradable polyurethane, and the biodegradable polyurethane comprises thermoplastic biodegradable polyurethane or crosslinked biodegradable polyurethane.

12. The method according to claim 11, wherein an operation process of the freeze-drying method comprises: storing polyurethane emulsion at 4° C. and removing gas in the emulsion; then standing at −20° C. for a night and then performing freeze-drying; and then performing drying;

an operation process of the electrostatic spinning method comprises: dissolving polyurethane in a mixed solvent of tetrahydrofuran and dimethylacetamide or in hexafluoroisopropanol, and performing electrospinning by using tin foil paper as a receiver to obtain a polyurethane electrospun fiber porous scaffold;

an operation process of the 3D printing method comprises: adding gelatin into polyurethane emulsion and performing 3D printing to obtain a polyurethane 3D printed porous scaffold;

an operation process of the particulate leaching method comprises: adding sodium chloride into polyurethane emulsion, then spreading solution on a smooth plane, allowing natural volatilization and then performing drying; and then using water to wash away sodium chloride particulates therein to obtain a polyurethane particulate leached porous scaffold; and an operation process of the gas foaming method comprises: drying polyurethane solution to obtain a thin film, then immersing the obtained thin film in supercritical carbon dioxide to a saturated state and finally decreasing pressure to a normal-pressure state to obtain a polyurethane gas foamed porous scaffold.

13. The method according to claim 2, wherein the compression modulus of the three-dimensional porous polyurethane is 0.1-3.0 MPa.

14. The method according to claim 5, wherein the porosity of the three-dimensional porous polyurethane is 70-90%.

15. The method according to claim 2, wherein the polyurethane comprises biodegradable polyurethane; and the biodegradable polyurethane comprises thermoplastic biodegradable polyurethane or crosslinked biodegradable polyurethane.

16. The method according to claim 3, wherein the polyurethane comprises biodegradable polyurethane; and the biodegradable polyurethane comprises thermoplastic biodegradable polyurethane or crosslinked biodegradable polyurethane.

17. The method according to claim 4, wherein the polyurethane comprises biodegradable polyurethane; and the biodegradable polyurethane comprises thermoplastic biodegradable polyurethane or crosslinked biodegradable polyurethane.

18. The method according to claim 5, wherein the polyurethane comprises biodegradable polyurethane; and the biodegradable polyurethane comprises thermoplastic biodegradable polyurethane or crosslinked biodegradable polyurethane.

19. The method according to claim 6, wherein the polyurethane comprises biodegradable polyurethane; and the biodegradable polyurethane comprises thermoplastic biodegradable polyurethane or crosslinked biodegradable polyurethane.

20. The method according to claim 2, wherein the scaffold further comprises a functional cell factor and/or a functional cell; and the functional cell factor comprises at least one of nerve growth factor, brain-derived neurotrophic factor and glia-derived neurotrophic factor.

* * * * *